US00PP31254P2

(12) United States Plant Patent
Hansen

(10) Patent No.: US PP31,254 P2
(45) Date of Patent: Dec. 17, 2019

(54) ***SALVIA* PLANT NAMED 'INDIGLO GIRL'**

(50) Latin Name: ***Salvia nemorosa* (Linnaeus)**
Varietal Denomination: Indiglo Girl

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 15/998,377

(22) Filed: Aug. 10, 2018

(51) Int. Cl.
*A01H 5/02* (2018.01)
*A01H 6/50* (2018.01)

(52) U.S. Cl.
USPC ..... Plt./475
CPC ..... *A01H 6/508* (2018.05)

(58) Field of Classification Search
USPC ..... Plt./475
See application file for complete search history.

*Primary Examiner* — Anne Marie Grunberg

(57) ABSTRACT

The new and distinct cultivar of perennial *Salvia* plant named 'Indiglo Girl' characterized by its large strong violet-colored flowers densely arranged in dense verticils, with upright habit and stiff, upright; heavily-branched stems and strong vigorous growth rate and large deep-green foliage. *Salvia* 'Indiglo Girl' is especially useful for landscaping and containerized ornamentals by itself or in combination with other plants.

2 Drawing Sheets

Botanical denomination: *Salvia nemorosa* (Linnaeus).
Cultivar designation: 'Indiglo Girl'.

BACKGROUND OF THE INVENTION

The present invention relates to a new and distinct cultivar of ornamental sage plant hereinafter referred to by the cultivar name *Salvia* 'Indiglo Girl' or as the new plant. The new plant was the result of a controlled pollination between the proprietary unreleased hybrid known only by the breeder code number *Salvia* 12-31-02 (not patented) (a seedling of 'Pink Dawn' U.S. Plant Pat. No. 26,343) as the female patent and 'Violet Riot' U.S. Plant Pat. No. 26,273 as the male parent at a wholesale perennial nursery in Zeeland, Mich., USA. The seeds were harvested in the fall of 2013 and the single specific seedling that developed into the new *Salvia* was assigned the breeder code 13-10-22 through the evaluation process. The new plant was first selected for further evaluation in the summer of 2014 and selected for final evaluation in the summer of 2016. The first asexual propagation was performed in the summer of 2014 by basal cuttings at the same nursery in Zeeland, Mich. 'Indiglo Girl' has proven that it is stable and reliably produces true to type plants in successive generations of asexual propagation.

No plants of *Salvia* 'Indiglo Girl' have been sold or disclosed in this country, or anywhere in the world, by this or any name, more than one year prior to the filing of this application, with the exception of that which was sold or disclosed either directly or indirectly from the inventor and within one year from the filing of this application.

SUMMARY OF THE INVENTION

Plants of *Salvia* 'Indiglo Girl' have not been observed under all possible environmental conditions. The phenotype may vary somewhat with variations in environment such as temperature, nutrition and light intensity without, however, any variance in genotype.

*Salvia* 'Indiglo Girl' can be most closely compared to 'Blue Marvel' U.S. Plant Pat. No. 27,018 and 'Midnight Model' U.S. Plant Pat. No. 29,498. 'Blue Marvel' is smaller in habit, the foliage is larger and the flower color is slightly different colored. 'Midnight Model' has darker colored flowers and is slightly taller in habit. The female parent, *Salvia* 12-31-02, has larger pink flowers and the habit is more spreading and less upright. The male parent has smaller, more violet flowers and more branching with smaller foliage. The new plant can also be compared to 'Haeumanarc' U.S. Plant Pat. No. 13,322 which is much shorter in habit with smaller and has a lighter bluish flower color. Compared with *Salvia* 'Bumbleblue' U.S. Plant patent application Ser. No. 15/731,914, the new plant is much larger in habit with larger leaves and flowers.

The following characteristics in combination distinguish *Saliva* 'Indiglo Girl' as a new and distinct cultivar:

1. Large, strong violet-colored flowers densely arranged in tight verticils;
2. Upright habit with stiff, upright, heavily-branched stems;
3. Strong, vigorous and winter-hardy;
4. Large, rugose, deep-green foliage.

BRIEF DESCRIPTION OF THE DRAWINGS

The photographs of the new plant demonstrate the unique traits and the overall appearance of *Salvia* 'Indiglo Girl'. The colors are as accurate as reasonably possible with color reproductions. Variation in ambient light spectrum, source and direction may cause the appearance of minor variation in color. The plant used in the photographs was a one-year old plant grown in an open, full-sun trial garden at a wholesale perennial nursery in Zeeland, Mich. with supplemental water and fertilizer when needed. No stem pinching or plant growth regulators have been used.

DETAILED BOTANICAL DESCRIPTION

Figure 1:
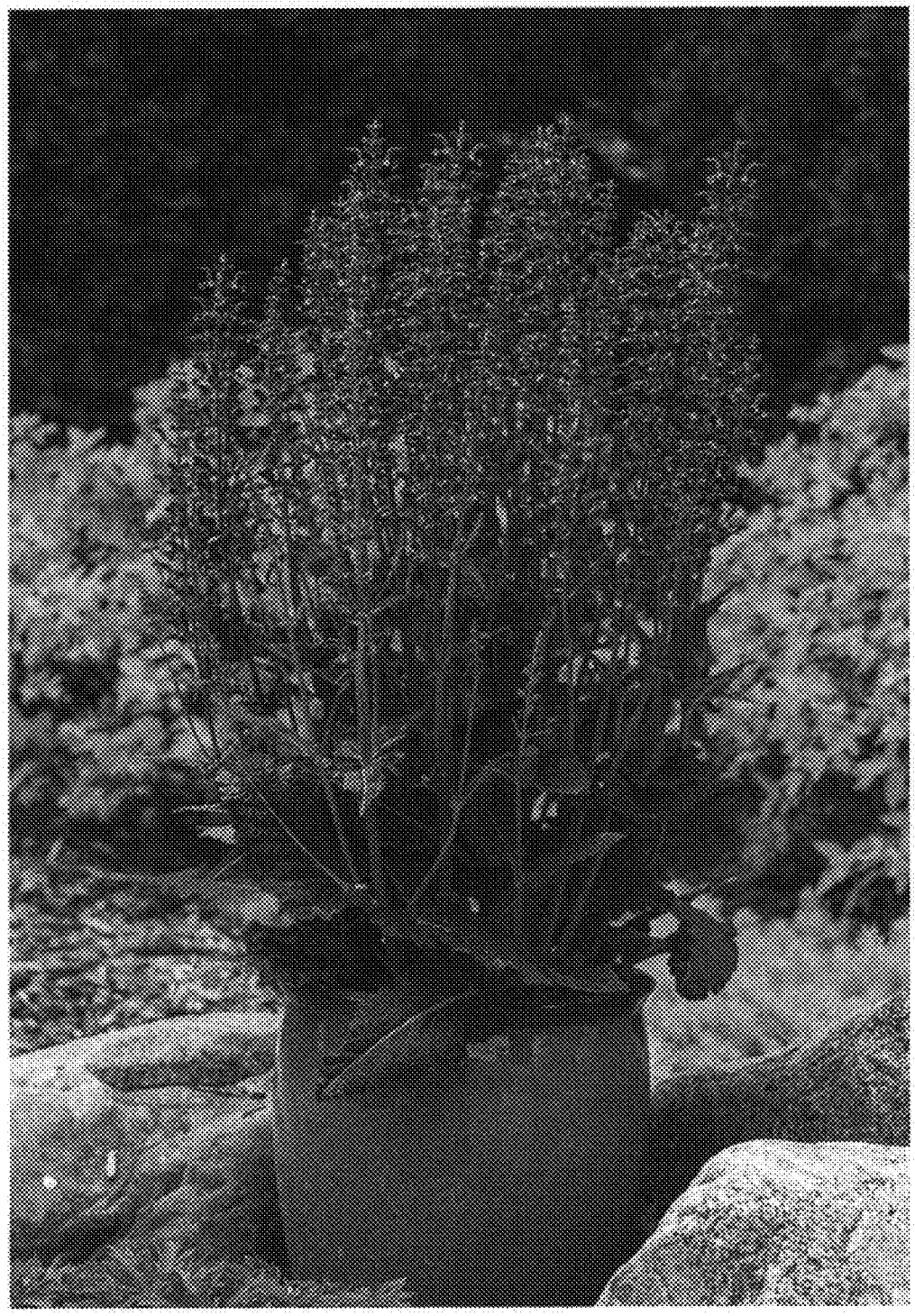
FIG. 1 shows the plant habit in full flower in a container.
Figure 2:
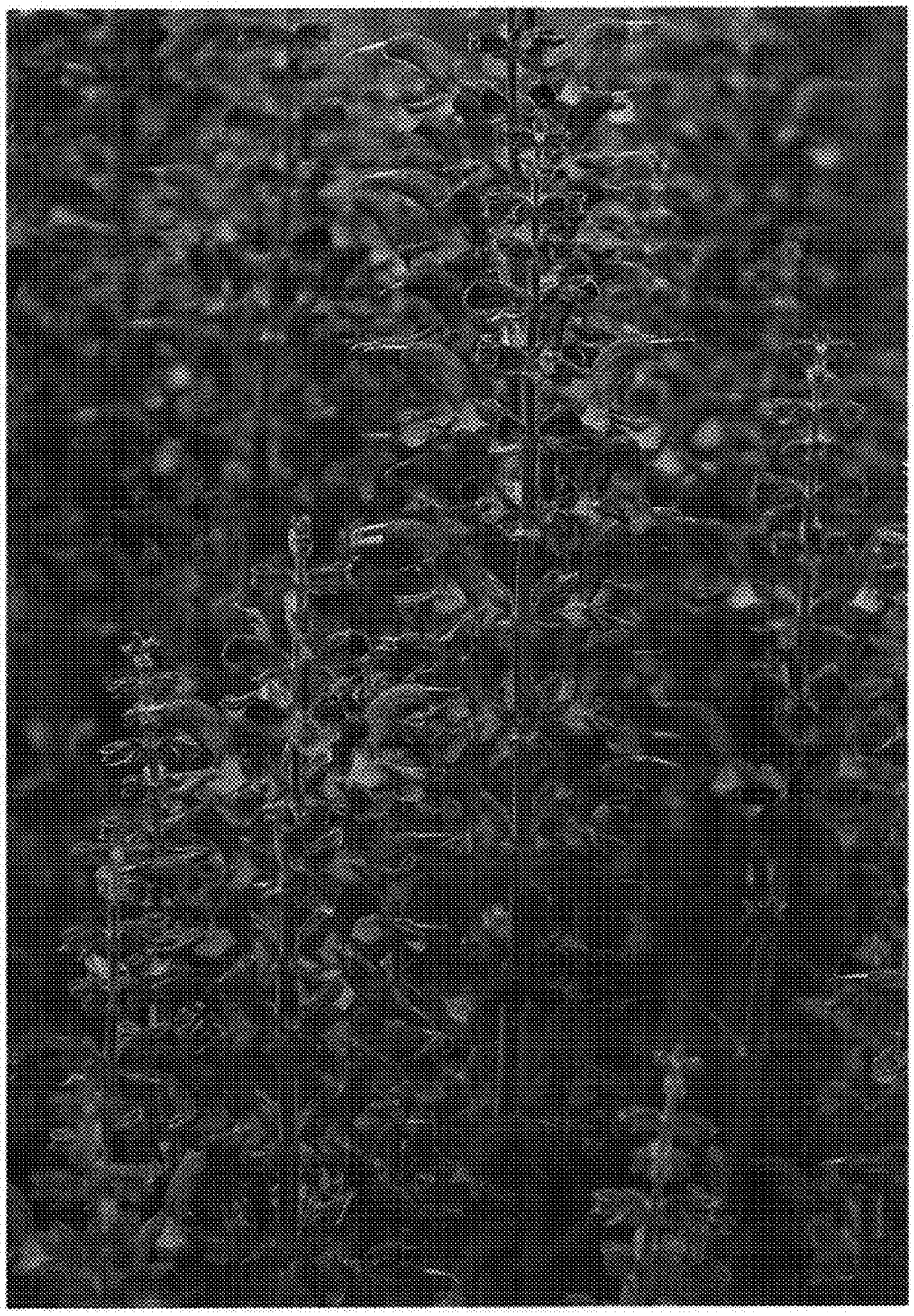
FIG. 2 shows a close-up of the flower scape with the buds and strong violet petal color.

The following descriptions and color references except where common dictionary terms are used are based on the 2015 edition of The Royal Horticultural Society Colour Chart. *Salvia* 'Indiglo Girl' has not been observed under all possible environments. The phenotype may vary slightly with different growing environments such as temperature, light, fertility, soil pH, moisture and plant maturity levels, but without any change in the genotype. The following observations and size descriptions are based on two-year old plants growing in a greenhouse with minimal shading in addition to two-year-old plants grown in a full-sun trial garden at a wholesale perennial nursery in Zeeland, Mich. Plants were given supplemental water and fertilizer but no plant growth regulators were used.

Botanical classification: *Salvia nemorosa* (Linnaeus);

Parentage: Female or seed parent is the unreleased non-patented proprietary hybrid 12-31-02; the male or pollen parent is 'Violet Riot';

Plant habit: Winter-hardy herbaceous perennial; multi-stemmed, with basal and cauline foliage, and flowers in several tightly arranged verticils on heavily-branched upright racemes displayed above foliage; in flower with panicles about 54.0 cm tall and about 48.0 cm wide at the fullest point about 10.0 cm above soil; foliage extends about two-thirds of the way up the stems;

Propagation: By herbaceous tip cuttings; time to produce a rooted stems about two weeks;

Growth rate: Rapid, vigorous, finishing in from a 25 mm plug to flower in one-gallon pot in about 8 to 10 weeks, and flowering in a one-gallon pot from a dormant bare-root one-year-old plant in about 6 to 8 weeks; vernalization not required but beneficial;

Root description: Fine, well-branched; color dependent on age and soil type, from cream to dark tan in color;

Foliage: Opposite, simple, rugose, ovate; margin crenate to lobed with lobes incised about 5.0 mm; glabrous adaxial and puberulent abaxial; acute apex and base cordate to rounded; leaf blades to about 17.0 cm long and 7.6 cm across, decreasing in size distally; average about 12.2 cm long and 2.2 cm across;

Foliage fragrance: Typical sage fragrance;

Foliage color: Mature adaxial surface nearest RHS 139A, mature abaxial surface nearest RHS NN137C; expanding adaxial nearest RHS 137B, expanding abaxial nearest RHS 138A;

Venation: Reticulate; impressed on adaxial side and ridged on abaxial side; puberulent abaxial, puberulent adaxial midrib and lightly puberulent adaxial secondary veins;

Vein color: Mature adaxial midrib blend between RHS 145D and RHS 147D, main and secondary veins nearest RHS 145C; mature abaxial midrib and main veins nearest RHS 145A, secondary veins nearest RHS 145B and developing to nearest RHS 147C toward margin; expanding adaxial midrib nearest RHS 145C and main and secondary veins nearest RHS 145C and developing to nearest RHS 145D; expanding abaxial midrib, main and secondary veins nearest RHS 147C;

Petiole: Concavo-convex, pubescent to puberulent abaxial and adaxial surfaces; to about 8.5 cm long and 4.0 mm wide at base, average 5.5 cm long and 3.0 mm wide at base;

Petiole color: Adaxial center blend between RHS 146D and RHS 148C, margins nearest RHS 146B; abaxial center lighter than RHS 146D and margins nearest RHS 146B;

Stems: Quadrangular; pubescent, to 16.0 cm long before flowers and 4.0 mm across at base;

Stem color: Nearest RHS 146B with light proximal blushing of nearest RHS N186A;

Nodes: Eight before flowering verticils; average internode length 2.2 cm; color same as stem;

Flower: Perfect; bilabiate; zygomorphic; verticillate with flowering generally beginning at lower verticils and advancing up the scape, not all flowers at same verticil opening at the same time, typically with about six flowers or buds per verticil; with lower lip projected outwardly almost horizontally and perpendicular to stem, and hood petal upwardly at about 45 degree angle above horizontal; self-cleaning, petals not persistent; flowering beginning late spring for about four weeks and repeating if initial scapes removed;

Flower longevity: About four days on the plant or as cut flower;

Flower fragrance: None detected;

Flower buds one to two days prior to anthesis: Shape is lightly falcate, with rounded apex; pubescent; about 14.0 mm long, 6.5 mm tall and 2.5 mm wide;

Flower bud color: Dorsal petals nearest RHS 90A and ventral petals RHS N88A; calyx nearest RHS 137B with occasional blushing on dorsal side of nearest RHS N186B, calyx veins nearest RHS 137A;

Flower size: About 20.0 cm long from base of calyx to tip of exserted style, 14.0 mm tall and 6.0 mm wide;

Petals: Bilabiate corolla; with upper hood and lower labium producing an angle between the two petals of about 50 degrees;

Hood (upper) petal: Distal portion slightly arcuate and laterally conduplicate with emarginate apex and basal 8.5 mm fused into tube about 2.5 mm diameter at base and about 5.0 mm diameter at petal separation; puberulent to glandular outside, glabrous inside; about 17.5 mm long, 5.0 mm tall and 1.5 mm across;

Labium (lower) petal: Consisting of three apical lobes, two upwardly projecting lateral lobes about 3.0 mm long and about 2.0 mm wide at base with rounded apex, one central lobe about 4.0 mm long 8.0 mm wide with rounded apex with crenulate margin; distal portion of lower labium slightly concaved upwards; distally glabrous adaxial; glabrous abaxial except puberulent along abaxial longitudinal axis; adaxial tube minutely puberulent in both dorsal and ventral portions; about 13.5 mm long, 8.0 mm wide at the widest portion and 5.0 mm tall;

Petal color: Abaxial distal hood nearest RHS 90A and lightening to lighter than RHS 91D at base of tube, adaxial distal hood nearest RHS 90B and proximal tube nearest RHS NN155D; adaxial and abaxial lower labium distally nearest RHS N89B, abaxial lower labium tube lightening proximally to nearest lighter than RHS 91D;

Androecium: Two, fused with labium, contained within hood petal; not fully developed;

*Filament*.—Glabrous, about 3.0 mm long and about 0.3 mm diameter; adnate about 8.0 mm from base of tube; curved around inside of hood petal; color nearest RHS 91D.

*Anther*.—Glabrous, oblong, about 1.8 mm long and about 0.5 mm diameter; longitudinal, dorsifixed; dorsal color between RHS N187B and RHS N187A, ventral nearest RHS NN155D.

*Pollen*.—Not observed.

Gynoecium: One, curved around inside of hood petal; total about 21.0 mm long;

*Style*.—About 19.0 mm long and less than 0.5 mm diameter; color nearest RHS NN155D at base, darkening distally to darker than RHS 86A before stigma split.

*Stigma*.—Split in two and curved in the terminal 2.0 mm; apex pointed; color nearest RHS N89A.

*Ovary*.—Superior; color nearest RHS 145A.

*Fruit*.—One to four nutlets per flower; ellipsoidal to spherical; about 1.5 mm across and 1.7 mm long; color nearest RHS 202A.

Calyx: Five sepals, three upper and two lower, campanulate, apex acute; fused in basal 5.0 mm; persistent; tube about 8.0 mm long and 3.5 mm wide; lower cleft about 3.0 mm deep between lobes and upper and lower set; upper set of three fused to closer than 1.0 mm of apex;

Calyx color: Abaxial nearest RHS 137B with veins nearest RHS 137A and occasionally lightly blushed with nearest RHS N187A; adaxial base nearest RHS 145D, distally nearest RHS 138C with darker veins of nearest RHS 138A;

Bracts: Each verticil subtended by two opposite bracts; apex acuminate, base truncate, shape nearly cordate; margin entire, ciliolate, and glabrous above and below; bract size up to 30.0 mm long and 17.0 mm wide, decreasing distally; color of both surfaces nearest RHS NN137A with center and base veins nearest RHS 145D;

Peduncles: Quadrangular in cross section, strong; upright; flowering portion to about 33.0 cm tall and 27.5 cm across with branches taller than central stem; main stem 5.0 mm across at base; finely puberulent; heavily branched with opposite branches at about 45 degrees above horizontal at the three nodes below flowers; branches to about 36.0 cm long and 3.0 mm across; average space between verticils about 1.4 cm;

Peduncle color: Nearest RHS 146B;

Pedicels: Cylindrical, about 3.0 mm long and 0.7 mm diameter; puberulent; to about 45 degrees above horizontal;

Pedicel color: Nearest RHS N144D proximally and lightly blushed with nearest RHS 186A distally;

Disease and pest resistance: Plants of *Salvia* 'Indiglo Girl' perform best with adequate moisture and good drainage but are fairly drought tolerant once established; hardy from at least USDA zone 3 to 8; resistance to diseases and pests beyond that common to *Salvia* has not been noted.

It is claimed:

1. The new and distinct perennial *Salvia* plant named 'Indiglo Girl' as herein described and illustrated useful for landscaping as a specimen plant, en masse or as a cut flower.

* * * * *